15

(12) United States Patent
Veldman et al.

(10) Patent No.: US 8,016,830 B2
(45) Date of Patent: Sep. 13, 2011

(54) DEVICES AND METHODS FOR GRASPING AN ELONGATED MEDICAL ELEMENT

(75) Inventors: Michael S. Veldman, Memphis, TN (US); Harold Sparr Taylor, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 849 days.

(21) Appl. No.: 11/335,389

(22) Filed: Jan. 19, 2006

(65) Prior Publication Data

US 2007/0171540 A1    Jul. 26, 2007

(51) Int. Cl.
*A61F 2/46* (2006.01)
*A61F 5/04* (2006.01)
*B43K 27/04* (2006.01)

(52) U.S. Cl. ............................. 606/86 R; 401/35; 606/53

(58) Field of Classification Search ............ 279/22, 279/82; 401/65; 604/57; 606/232, 148, 606/80, 86 A, 86 B, 86 R, 87–98, 167–174; 24/115 R See application file for complete search history.

(56) References Cited

U.S. PATENT DOCUMENTS

| 2,287,364 | A | * | 6/1942 | Wehn ................................ 401/74 |
| 2,733,926 | A | * | 2/1956 | Colton W.G. ...................... 279/75 |
| 3,524,227 | A | * | 8/1970 | Kelly ............................ 24/115 R |
| 3,631,597 | A | * | 1/1972 | Lieb et al. ...................... 433/129 |
| 3,758,922 | A | * | 9/1973 | Field ............................ 24/136 R |
| 3,868,748 | A | * | 3/1975 | Kelly ............................ 24/115 M |
| 4,106,836 | A |   | 8/1978 | Asick et al. |
| 4,171,170 | A | * | 10/1979 | Kageyama et al. ............. 401/65 |
| 4,202,557 | A | * | 5/1980 | Haussmann et al. ......... 279/19.5 |
| 4,687,363 | A | * | 8/1987 | Kageyama ........................ 401/65 |
| 4,744,788 | A | * | 5/1988 | Mercer, Jr. ...................... 604/500 |
| 4,872,776 | A | * | 10/1989 | Kageyama et al. ............. 401/65 |
| 4,881,302 | A | * | 11/1989 | Lee ............................ 24/136 R |
| 4,966,600 | A |   | 10/1990 | Songer et al. |
| 5,052,838 | A | * | 10/1991 | Tucker ............................ 401/65 |
| 5,109,867 | A | * | 5/1992 | Twyford, Jr. .................. 600/585 |
| 5,116,340 | A |   | 5/1992 | Songer et al. |
| 5,222,956 | A | * | 6/1993 | Waldron ......................... 606/80 |
| 5,318,566 | A |   | 6/1994 | Miller |
| 5,395,374 | A |   | 3/1995 | Miller et al. |
| 5,449,361 | A |   | 9/1995 | Preissman |
| 5,476,465 | A |   | 12/1995 | Preissman |
| 5,490,683 | A | * | 2/1996 | Mickel et al. ................... 279/75 |
| 5,499,985 | A | * | 3/1996 | Hein et al. ...................... 606/99 |
| 5,540,698 | A |   | 7/1996 | Preissman |
| 5,681,351 | A | * | 10/1997 | Jamiolkowski et al. ...... 606/232 |

(Continued)

FOREIGN PATENT DOCUMENTS

EP           0577219 A1      1/1994

*Primary Examiner* — Thomas C Barrett
*Assistant Examiner* — Matthew Lawson

(57) ABSTRACT

Devices to grasp a medical element that may include a first member, a second member that fits within the first member, and a locking element. The first and second members may move relative to one another to move the locking element between locked and unlocked positions. In an unlocked position, the device may move along the element. In the locked position, the device may lock to the element and motion is prevented. In one application, the device can be placed in the locked position to maintain a desired amount of tension on the element. Methods of grasping the medical element may include moving the first and second members relative to each other thereby moving the locking element to grasp and release the medical element.

22 Claims, 7 Drawing Sheets

U.S. PATENT DOCUMENTS

| | | | |
|---|---|---|---|
| 5,827,000 A * | 10/1998 | Andrews | 401/65 |
| 5,928,241 A * | 7/1999 | Menut et al. | 606/80 |
| 6,000,940 A * | 12/1999 | Buss et al. | 433/127 |
| 6,099,527 A | 8/2000 | Hochschuler et al. | |
| 6,152,941 A * | 11/2000 | Himes et al. | 606/180 |
| 6,176,817 B1 | 1/2001 | Carey et al. | |
| 6,241,410 B1 * | 6/2001 | Hager | 401/89 |
| 6,270,087 B1 * | 8/2001 | Mickel et al. | 279/75 |
| 6,347,914 B1 * | 2/2002 | Boyle et al. | 408/240 |
| 6,695,321 B2 * | 2/2004 | Bedi et al. | 279/22 |
| 6,722,667 B2 * | 4/2004 | Cantlon | 279/22 |
| 6,783,528 B2 * | 8/2004 | Vincent-Prestigiacomo | 606/246 |
| 6,793,429 B2 * | 9/2004 | Arrison | 401/93 |
| 6,929,266 B2 * | 8/2005 | Peters et al. | 279/82 |
| 7,066,940 B2 * | 6/2006 | Riedel et al. | 606/79 |
| 7,232,270 B1 * | 6/2007 | Goldstein | 401/93 |
| 7,322,982 B2 * | 1/2008 | Vincent-Prestigiacomo | 606/246 |
| 2002/0082565 A1 * | 6/2002 | Bardani | 604/239 |
| 2002/0151902 A1 * | 10/2002 | Riedel et al. | 606/80 |
| 2003/0130663 A1 * | 7/2003 | Walen | 606/80 |
| 2003/0230862 A1 * | 12/2003 | Peters et al. | 279/82 |
| 2007/0005077 A1 * | 1/2007 | Null et al. | 606/104 |
| 2007/0123891 A1 * | 5/2007 | Ries et al. | 606/80 |
| 2007/0172299 A1 * | 7/2007 | Franck et al. | 401/92 |
| 2008/0195220 A1 * | 8/2008 | Pope et al. | 623/22.17 |

* cited by examiner

US 8,016,830 B2

DEVICES AND METHODS FOR GRASPING AN ELONGATED MEDICAL ELEMENT

BACKGROUND

The present application relates generally to devices and methods for securing an elongated element, and particularly to devices and methods for grasping a medical element and/or maintain tension on the medical element.

Elongated elements, including cables, rods, and fasteners, are used in a variety of surgical procedures. The spine is one area of the body that uses elongated elements in many of the surgical procedures. Spinal surgical procedures that use elongated elements may include spinal trauma surgery, reconstructive spinal surgery, and spinal fusions. Elongated elements are also used in surgical procedures affecting other areas of the body.

It may be difficult to grasp and control the elongated element during the surgical procedure. Elements may include a small size making them difficult to manually grasp. Elements may further be exposed to bodily fluids making them slippery and even more difficult to grasp. Further, the element may be positioned at an inaccessible location within the patient during the surgical procedure.

Elements are often used in surgical procedures that require application of a tension force. One example is a tensioning element that spans across two or more vertebral elements. A first end of the element is attached to a first vertebral member and is placed in tension. While the element remains in tension, a second end of the element is attached to a second vertebral member. It is often difficult to maintain the element in tension and secure the second end.

SUMMARY

The present application is directed to devices and methods to grasp an elongated medical element. In one embodiment, the device includes a first member, a second member that fits within the first member, and a locking mechanism. The first and second members may move relative to one another to move the mechanism between unlocked and locked positions. The first and second members may be configured for the element to extend through an interior section of each. In one embodiment in an unlocked position, the device moves along the element. In one embodiment of the locked position, the device locks to the element and motion is prevented. In one usage, the device can be placed in the locked position to maintain a desired amount of tension on the element.

DETAILED DESCRIPTION

The present application is directed to devices and methods to grasp an elongated medical element. In one embodiment, the device is movable between unlocked and locked positions. In the unlocked position, the device may be movable along the elongated element. In the locked position, the device may be fixedly connected to the elongated element.

Figure 1:
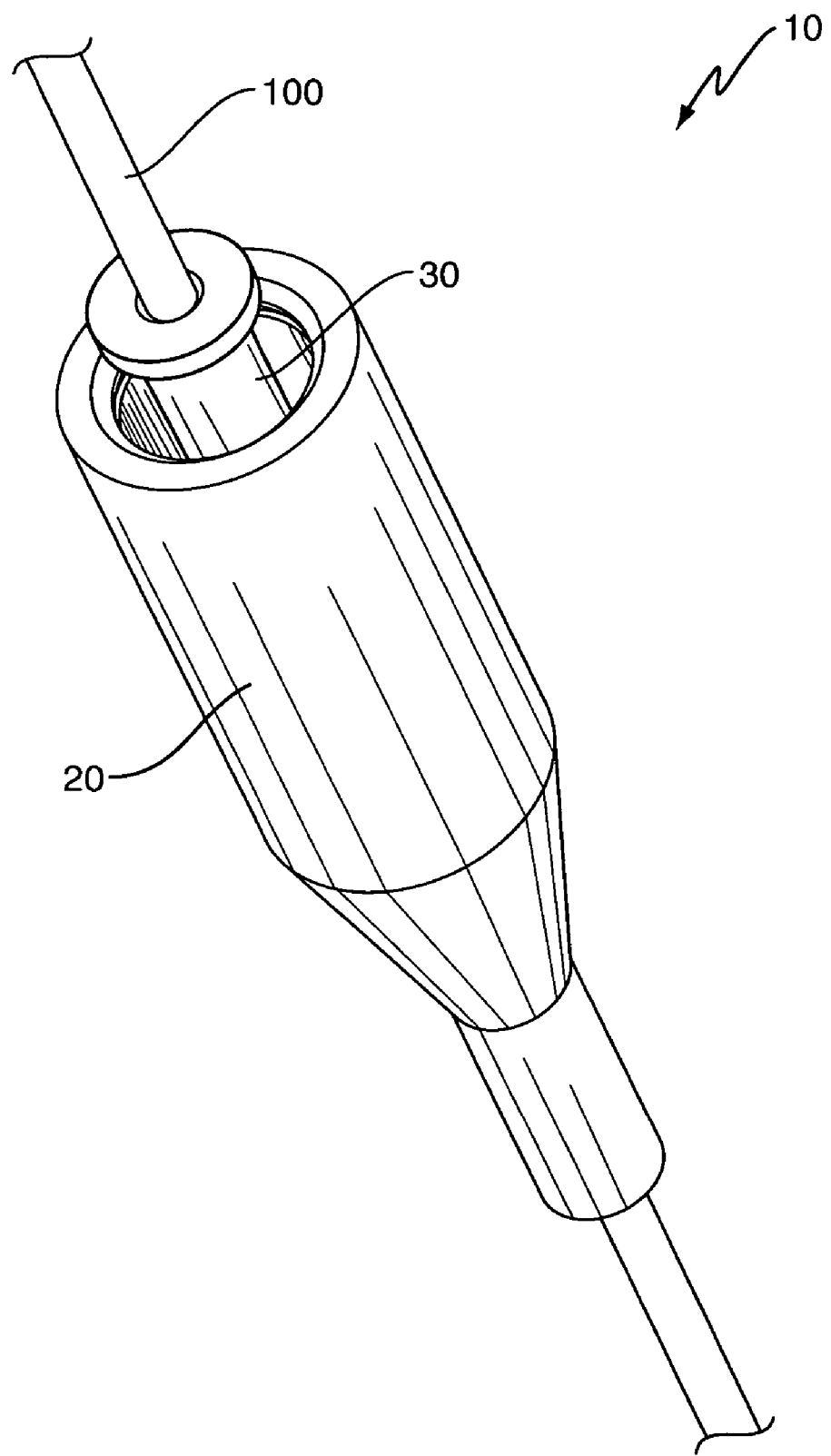
FIG. 1 is a perspective view of a device according to one embodiment.

One embodiment of a device is generally illustrated as element 10 in FIG. 1. The device 10 comprises a first member 20, a second member 30, and a lock 40 (see FIG. 2). In one embodiment, the second member 30 movably fits within the first member 20 to selectively engage and disengage the lock 40. In an unlocked position of one embodiment, the device 10 moves along the element 100. In a locked position of one embodiment, the device 10 locks to the element 100 and motion is prevented. In one application, the device 10 can be placed in the locked position to maintain a desired amount of tension on the element 100.

The term "elongated element" and the like is used generally herein to refer to cables, wires, rods, and fastener shafts. Embodiments of the element may be constructed to be flexible or inflexible, and include a variety of different cross-sectional shapes. Element embodiments may be solid, or may include a hollow interior. Embodiments may further include monofilament and single strand wire along with multi-filament and multi-strand cable and ropes. Specific embodiments include cables and rods used for securing together vertebral members. Another specific embodiment includes a shaft of a screw.

Figure 2:
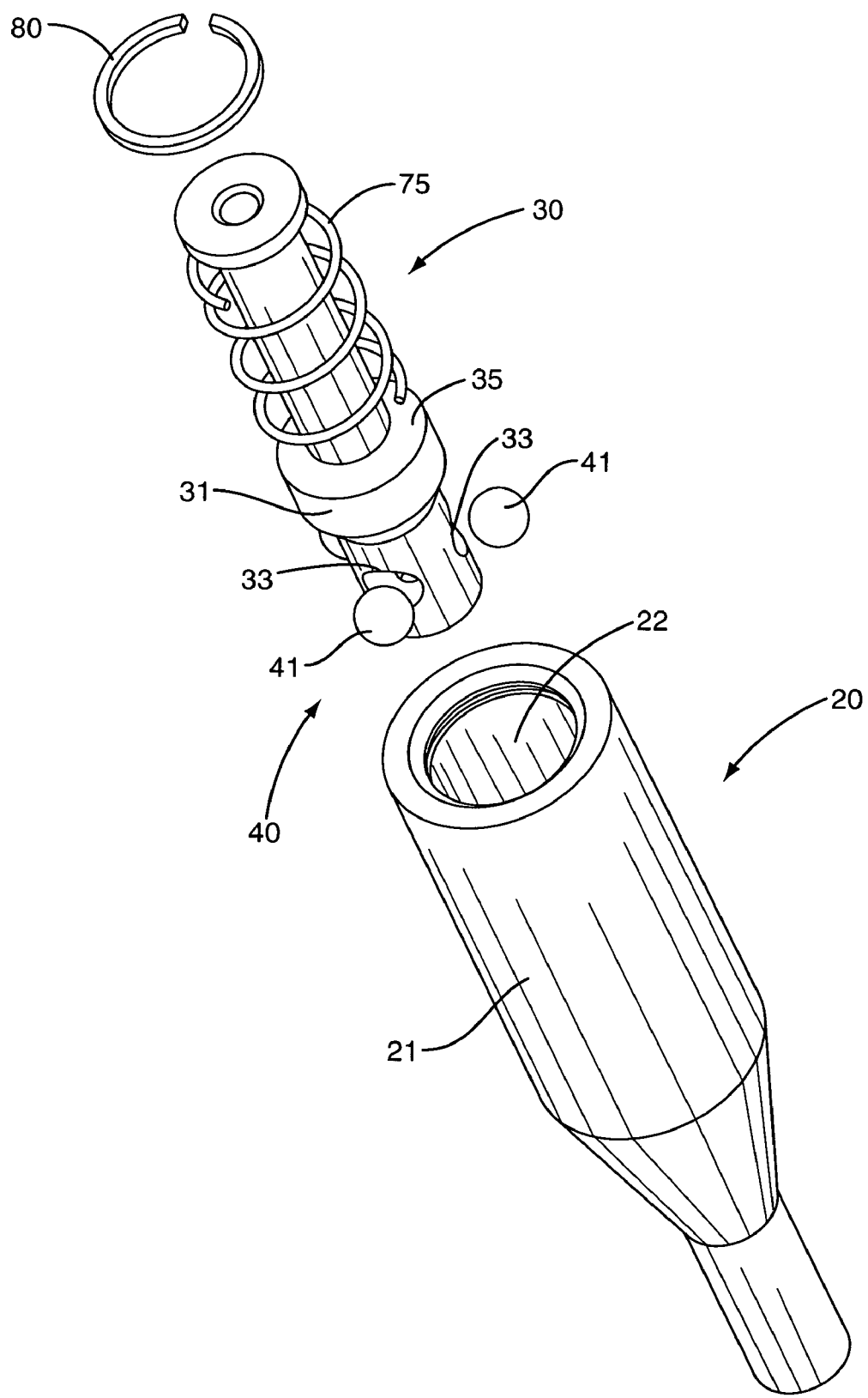
FIG. 2 is an exploded perspective view of a device according to one embodiment.

FIG. 2 illustrates an exploded view of one embodiment of a device 10 with the first member 20 sized to receive the second member 30. First member 20 in one embodiment includes a hollow body 21 having an open interior 22 that extends through the length. One embodiment of the second member 30 includes a body 31 having one or more openings 33 in a lower section. One embodiment of the lock 40 includes one or more locking elements 41 that fit within the openings 33. Locking elements 41 may move within the openings 33 between the locked and unlocked positions.

Figure 3:
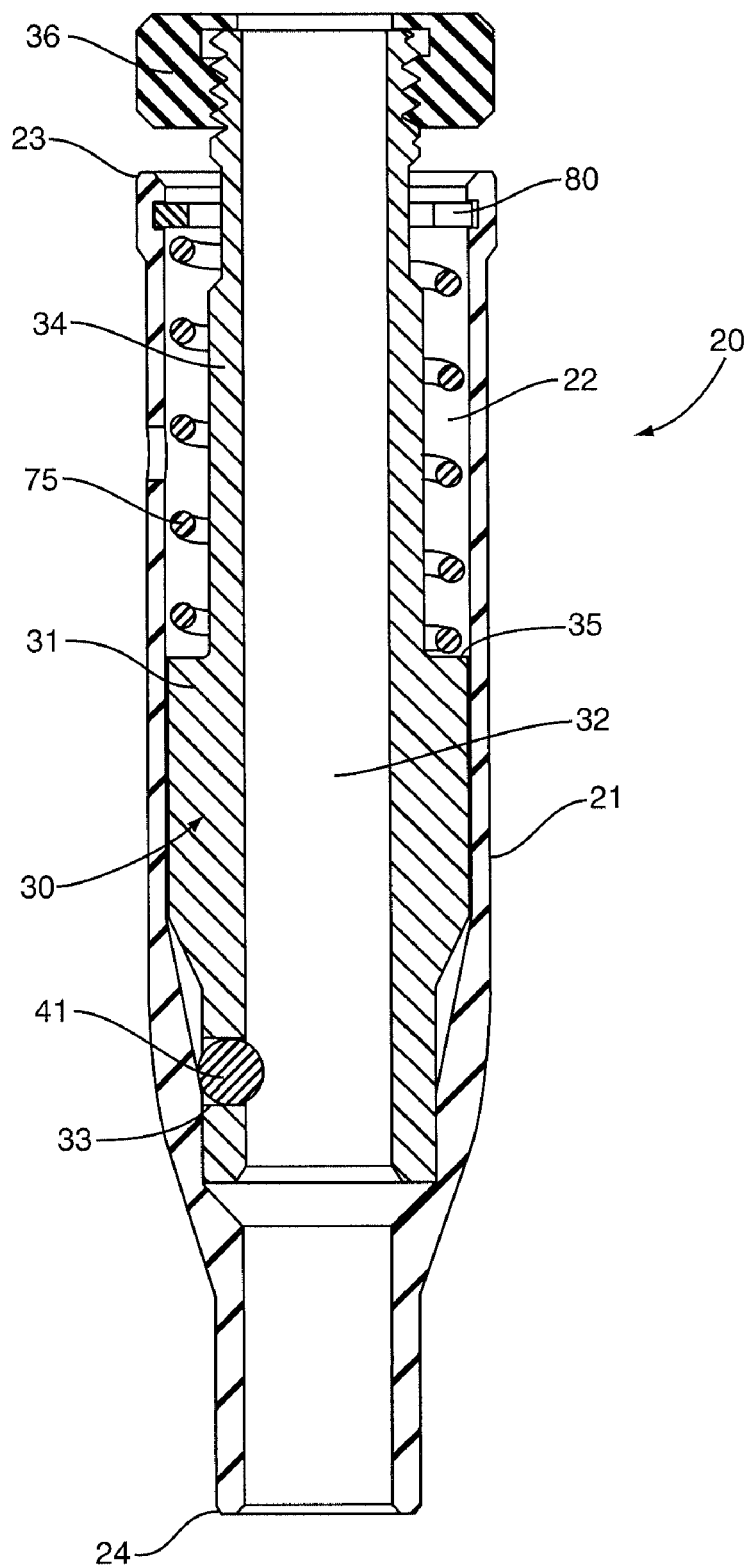
FIG. 3 is a cross-section lengthwise view of a device according to one embodiment.

FIG. 3 illustrates one embodiment of the device 10 with the element 100 removed for clarity. In this embodiment, the body 21 includes an elongated length extending between a first end 23 and a second end 24. In another embodiment, body 21 includes a smaller length extending around the element 100. Body 21 may be hollow forming the interior section 22 that extends the length. In one embodiment, body 21 includes a substantially circular cross-sectional shape with the interior section 22 also being substantially circular. In other embodiments, body 21 and the interior section 22 include non-circular cross-sectional shapes. In one embodiment, the interior section 22 includes a tapered shape with a width extending between inner sidewalls being greater towards the first end 23 and gradually reducing towards the second end 24. In one embodiment, the interior section 22 may include a constant taper throughout the length. In another embodiment, a taper extends along a discrete length of the interior section 22. In the embodiment illustrated in FIG. 3, the width is substantially constant inward from the first end 23 with a tapered section positioned towards the second end 24. In another embodiment, tapered section is positioned towards the first end 23. The taper may include a substantially continuous slope, or include different slopes along the length.

In one embodiment, the second member 30 includes body 31 sized to fit within the interior section 22. In one embodiment, a limited section of the second member 30 fits within the interior section 22. In one embodiment as illustrated in FIG. 3, body 31 includes an interior section 32 that extends the length and is sized to receive the element 100. One or more openings 33 may extend through the body 31 and each is sized to receive a locking element 41. Openings 33 may be positioned along the length of the body 31 at a variety of locations. In one embodiment as illustrated in FIG. 3, openings 33 are positioned at a lower section of the body 31 to interact with the tapered section of body 21 as will be explained in detail below. In one embodiment, a single opening 33 is positioned within the body 31. In one embodiment, the body 31 includes three openings 33 that are radially aligned within a common plane and spaced about 120° apart around the body 31.

One embodiment of the body 31 further includes a neck section 34 with a reduced width to be spaced inward from the inner sidewalls of body 21. A shelf 35 having a larger width is positioned at one end of the neck section 34 in one embodiment. A cap 36 may be positioned at an upper end of the body 31.

In one embodiment, the lock 40 includes one or more locking elements 41 movably positioned at the openings 33. In one embodiment, locking elements 41 comprise spherical balls, such as ball bearings. In another embodiment, locking elements 41 include other shapes. In embodiments having plural locking elements 41, each of the elements 41 may include the same or different shapes and sizes. In one embodiment, each locking element 41 travels back and forth relative to the opening 33. As illustrated in the embodiment of FIG. 3, a thickness of the locking element 41 is greater than a thickness of the body 31 forming the opening 33 (other sections of the body 31 may include a greater thickness than the locking element). Therefore, downward movement of the second member 30 relative to the first member 20 causes the locking elements 41 to move radially inward when sliding along the tapered interior section 21.

Figure 4:
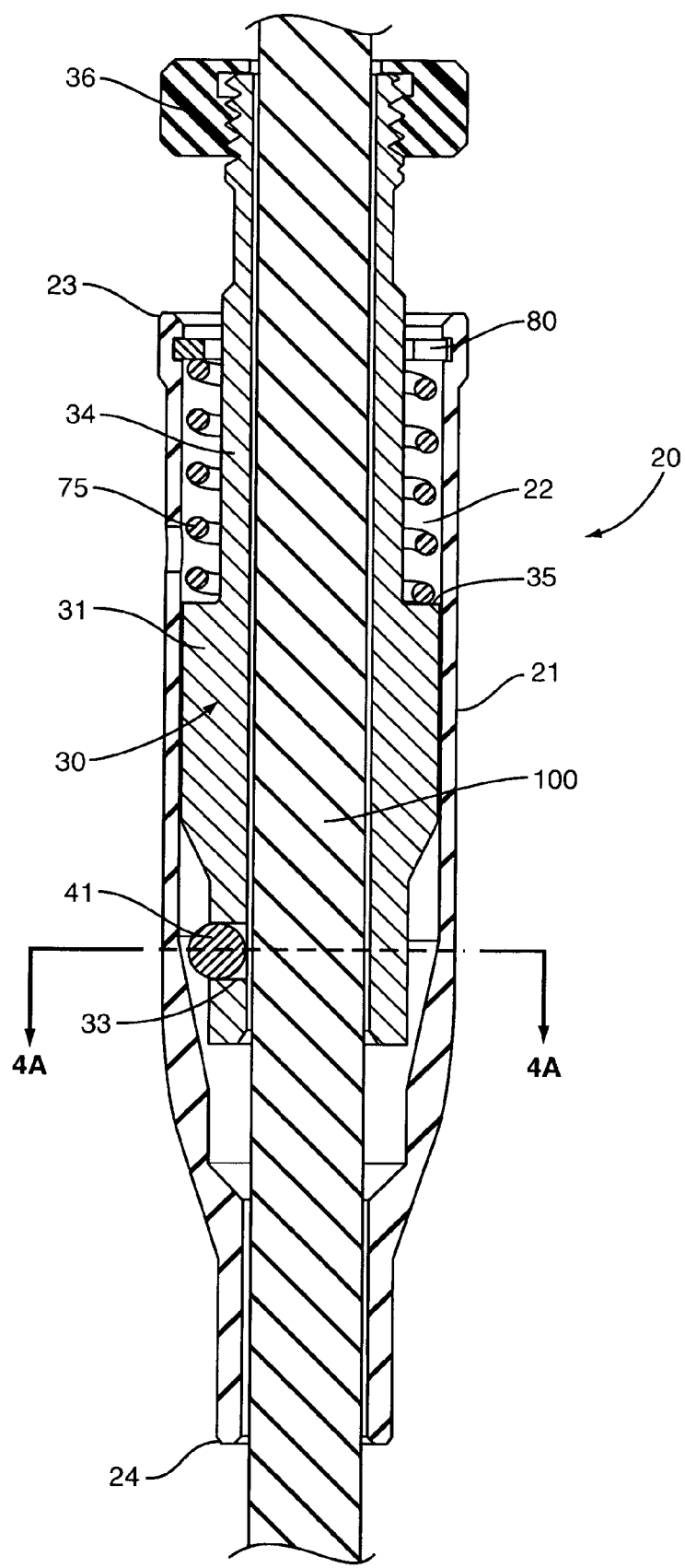
FIG. 4 is a cross-section lengthwise view of a device in an unlocked position according to one embodiment.

The number of locking elements 41 may vary depending upon the application. In one embodiment, a single locking element 41 locks the device 10. Other embodiments feature multiple locking elements 41. For embodiments with multiple locking elements 41, the elements 41 may be positioned within the same plane relative to the element 100. In other embodiments, two or more of the locking elements 41 may be positioned within different planes. Locking elements 41 may further include a variety of shapes and sizes. One embodiment as illustrated in FIG. 4 includes the locking element 41 having a spherical shape that moves within the openings 33. Another embodiment such as that illustrated in FIG. 6 includes the locking element 41 having a different shape.

Figure 6:
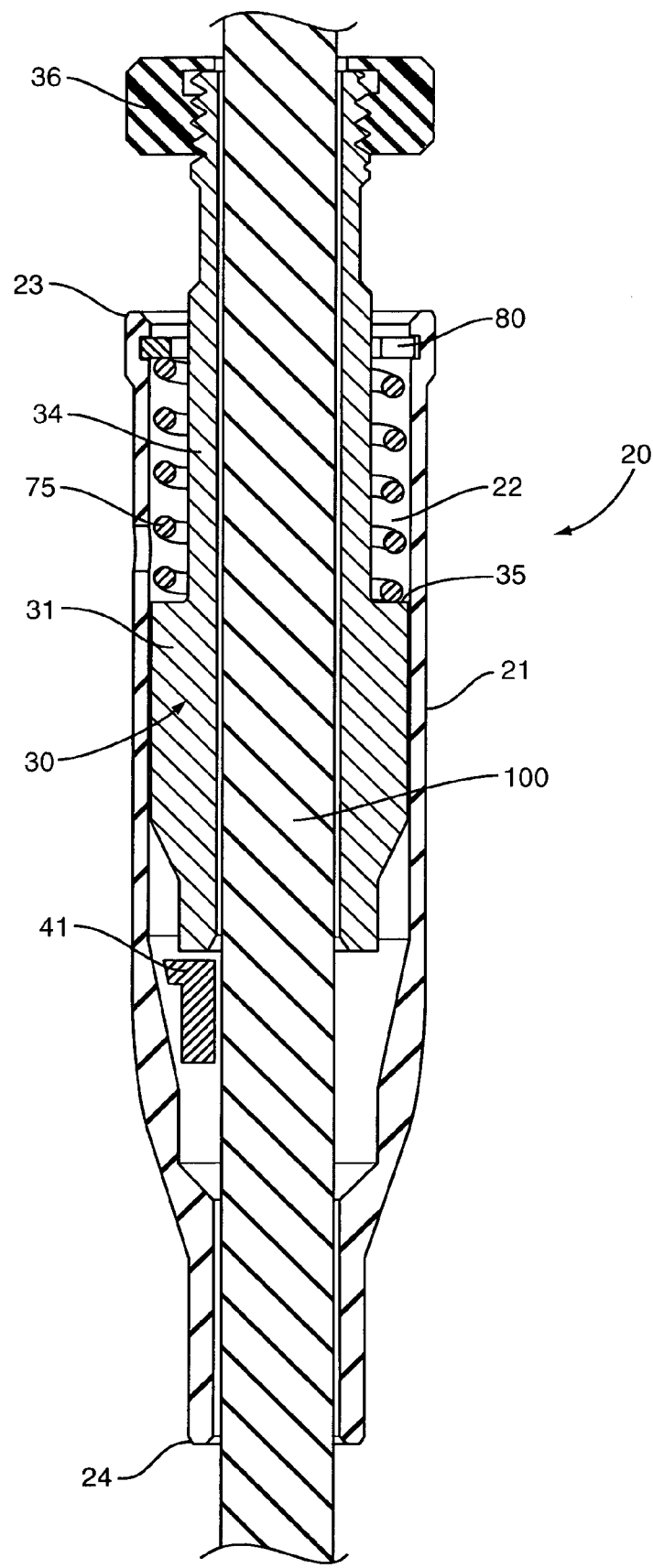
FIG. 6 is a cross-section lengthwise view of a device according to one embodiment.

In one embodiment, locking element 41 is contained within an opening 33 within the second member 30. In another embodiment as illustrated in FIG. 6, locking element 41 is positioned outside of the second member 30 and at a position to be contacted by the second member 30. Locking element 41 may be operatively connected to the second member 30, or may be unconnected.

FIG. 4 illustrates one embodiment in the unlocked position. In this embodiment, element 100 extends through the hollow interiors 22, 32 of the first and second members 20, 30. In one embodiment, element 100 is aligned with a centerline of a longitudinal axis that extends through the members 20, 30. The second member 30 is positioned within the first member 20 with the opening 33 positioned at a point where the interior section 22 is relatively wide. In one embodiment, a space formed between the element 100 and the sidewall of the interior section 22 is greater than the thickness of the locking elements 41 allowing the locking elements 41 to freely move thus preventing binding with the element 100.

Figure 4A:
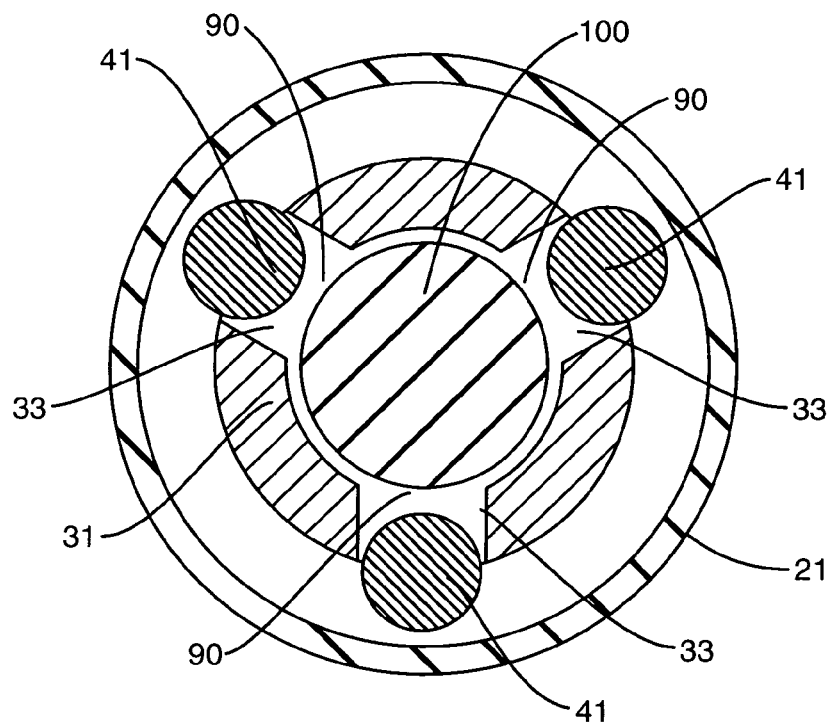
FIG. 4A is a cross-section view of the device of FIG. 4 cut along line 4A—4A.

FIG. 4A is a cross-sectional view of the device of FIG. 4 cut along line 4A—4A. In this embodiment, space 90 formed between the element 100 and the interior sidewall of the body 21 is greater than the thickness of the locking elements 41. Thus, the locking elements 41 may move within the space 90 and the element 100 may move within the device 10.

Figure 5:
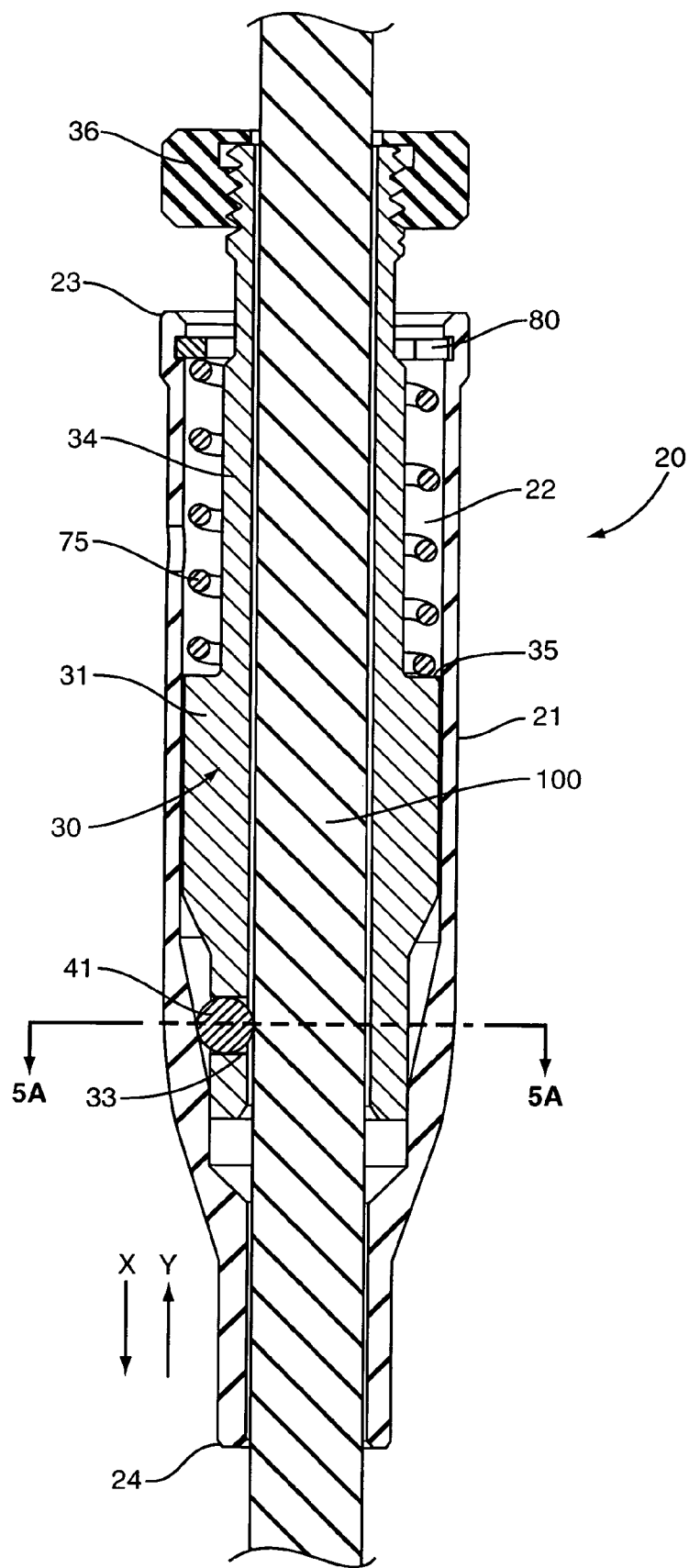
FIG. 5 is a cross-section lengthwise view of a device in a locked position according to one embodiment.
Figure 5A:
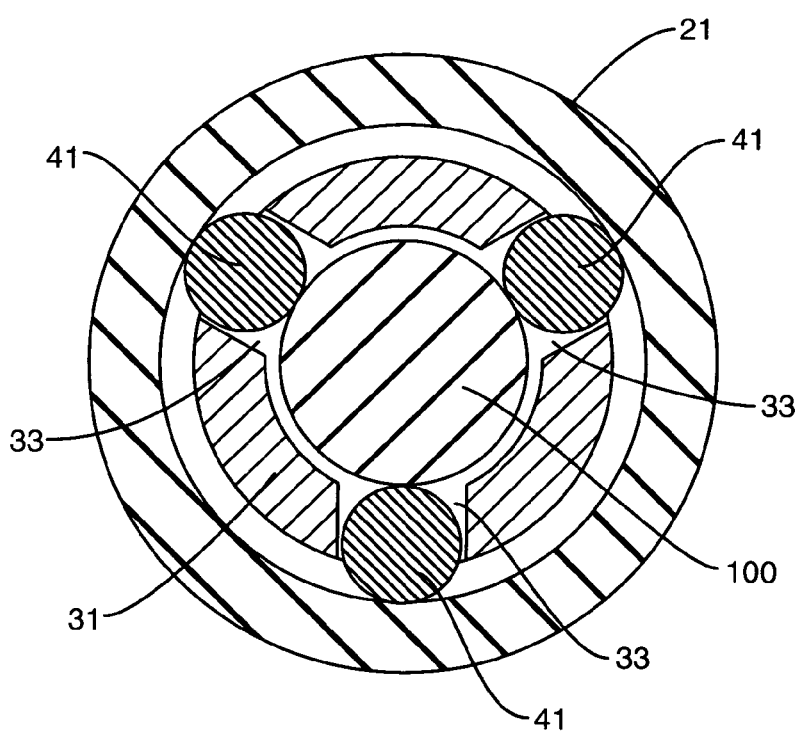
FIG. 5A is a cross-section view of the device of FIG. 5 cut along line 5A—5A.

FIGS. 5 and 5A illustrate one embodiment of a device in the locked position. In this embodiment, the second member 30 may be moved downward within the first member 20. Openings 33 are now aligned at a point where the space 90 formed between the element 100 and the sidewall of the interior section 22 is less than the thickness of the locking elements 41. This causes the locking elements 41 to extend inward through the openings 33 and into contact with the element 100. In one embodiment, this contact locks the device 10 to the element 100 and prevents relative movement.

In one embodiment, the tapered configuration results in a decreasing width of the interior section 22. Therefore, the locking elements 41 may apply a greater force on the element 100 the further the second member 30 is inserted downward into the first member 20. In one embodiment, the tapered configuration also accommodates elements 100 of different sizes. In one embodiment, an element 100 having a smaller width requires further insertion of the second member 30 into the first member 20, than does a element 100 having a larger width.

In one embodiment, a biasing mechanism 75 is positioned between the first and second members 20, 30. In one embodiment, a first end of the biasing mechanism 75 contacts the shelf 35 of the second member 30. In one embodiment, a washer 80 attached to the inner wall of the first member 20 forms a contact surface for a second end of the biasing mechanism 75. The biasing mechanism 75 in one embodiment includes a cylindrical configuration that is disposed around the neck 34. In one specific embodiment, biasing mechanism 75 is a coil spring. In one embodiment, biasing mechanism 75 applies a force on the second member 30 to maintain the device towards the locked position. The force may be adequate to lock the device, or may not be adequate to lock the device. Unlocking the device 10 may require moving the second member 30 away from the first member 20. In one embodiment, the pulling force is applied by grasping and pulling the cap 36, and moving the second member 30 upward to a point having a larger interior width.

Operation of one embodiment includes threading the element 100 through the interior sections 22, 32 of the first and second members 20, 30. The threading may occur before or after the second member 30 is inserted in the first member 20. After threading, the second member 30 is positioned in the unlocked configuration to allow for the device 10 to move along the length of the element 100. At the desired location, second member 30 is moved relative to the first member 20 thereby placing the locking elements 41 in the locked position against the element 100. In one embodiment, this prevents further movement of the device 10 along the element 100.

In one embodiment, the configuration of the device 10 may allow movement of the device in a first direction along the element 100, and prevent movement in a second direction. Using FIG. 5 as an example, grasping and moving the first member 20 in a longitudinal direction marked by arrow X causes the first member 20 to separate from the second member 30. In one embodiment, this causes the locking elements 41 to move to a point within the first member 20 having a larger width of the interior section 22 thereby preventing locking. In one embodiment, grasping the first member 20 and providing movement in a second longitudinal direction Y urges the second member 30 into the first member 20. This may move the locking elements 41 towards the locked position and prevent further movement of the device in the Y direction. In one embodiment, movement in the Y direction requires the second member 30 to be manually moved away from the first member 20.

Spatially relative terms such as "under", "below", "lower", "over", "upper", and the like, are used for ease of description to explain the positioning of one element relative to a second element. Further, the terms "down", "downward", "up", "upward", and the like, are used to explain the positioning of the elements as viewed in the Figures. These terms are intended to encompass different orientations of the device in addition to different orientations than those depicted in the figures. Further, terms such as "first", "second", and the like, are also used to describe various elements, regions, sections, etc and are also not intended to be limiting. Element numbers may be repeated in the different Figures to represent common elements between the many embodiments.

The present invention may be carried out in other ways than those specifically set forth herein without departing from essential characteristics of the invention. The present embodiments are to be considered in all respects as illustrative and not restrictive, and all changes coming within the meaning and equivalency range of the appended claims are intended to be embraced therein.

What is claimed is:

1. A medical device comprising:
a flexible elongated element with a first end and a second end;
an attachment member that extends around a section of the elongated element with the first and second ends extending outward from opposing sides, the attachment member comprising:
an outer member that includes a hollow interior;
an inner member sized to fit within the hollow interior of the outer member, the inner member being displaceable longitudinally in first and second directions relative to the outer member, the inner member further having a longitudinal channel that extends a length of the inner member for the element to pass through the inner member, the inner member also including a lateral opening into the channel;
an enlarged flange on the inner member that includes a width greater than the hollow interior of the outer member, the enlarged flange including a central opening for the element to pass through; and
a locking element disposed at least partly within the lateral opening and movable with respect thereto;
displacement of the inner member in the first direction with the locking element contacting against the outer member forces the locking element inward toward the channel to lock the attachment member to the element with the enlarged flange spaced a first distance from the outer member;
displacement of the inner member in the second direction allows the locking element to be outwardly displaced away from the channel to unlock the attachment member from the element for the attachment member to move along the element with the enlarged flange a greater distance than the first distance from the outer member.

2. The device of claim 1, wherein the locking element includes a spherical shape having a diameter that is greater than a width of the lateral opening.

3. The device of claim 1, wherein a section of the inner member extends outward from the outer member.

4. The device of claim 1, wherein the outer member includes a tapered inner wall with displacement of the inner member in the first direction moving the locking element into a narrowed section of the outer member and displacement in the second direction moving the locking element into an enlarged section of the outer member.

5. The device of claim 1, wherein the lateral opening is substantially perpendicular to the channel.

6. A medical device comprising:
an elongated element;
an attachment member comprising:
an outer member having a longitudinal first channel therethrough, said first channel having a tapered interior wall section;
an inner member disposed at least partially in the first channel and having a second longitudinal channel therethrough sized to receive the element; and
a locking element contained within the outer member, said locking element at least partially disposed in an opening that extends through a sidewall of the inner member;
the inner member moveable relative to the outer member between first and second positions, movement of the inner member from the first position to the second position forces the locking element to move inward relative to the second channel with the locking element in contact with the outer member;
the elongated element extending completely through both the outer and inner members and being in contact with the outer and inner members in both the first and second positions.

7. A medical device comprising:
an attachment member comprising:
a first member having a tapered interior wall;
a second member sized to fit at least partially within the first member;
a locking element movably contained within an opening that extends through a sidewall of the second member; and
a channel that extends completely through the attachment member and is formed from a first channel that extends through the first member and a second channel that extends through the second member;
an elongated element that extends through the channel and contacts against both the first and second members, the element includes a first end positioned outward from a first side of the attachment member and a second end positioned outward from a second side of the attachment member;
the second member being displaceable longitudinally in first and second directions relative to the first member with displacement of the second member in the first direction causing the locking element to contact against the first member and forcing the locking element laterally toward the channel and displacement of the second member in the second direction allows the locking element to be laterally displaced away from the channel.

8. The device of claim 7, wherein the first and second members each include a cylindrical shape with the element positioned within the members and along longitudinal axes of the members.

9. The device of claim 7, wherein the locking element includes a width larger than the opening.

10. The device of claim 7, wherein the locking element is a spherical member sized to move within the opening.

11. The device of claim 7, further comprising a second locking element movably contained within a second opening that extends through the sidewall of the second member, the second locking element being aligned within a common vertical plane with the locking element.

12. A medical device comprising:
a first tubular member having a tapered interior section;
a second tubular member including a first section sized to fit within the interior section in an overlapping arrangement and a second section wider than the interior section to prevent insertion into the interior section;
a locking element positioned within the interior section and contained within the first member; and
a channel extending longitudinally through the first member and the second member;
an elongated element that extends completely through the channel and includes a greater length than each of the first and second members;
the second member longitudinally movable within the first member between a first position with the locking element contacting the first member and extending into the channel and a second position with the locking element positioned away from the channel;
the element positioned directly next to both the first and second members in both the first and second positions.

13. The device of claim 12, wherein the interior section of the first member is tapered forming a first level with a first width and a second level with a second larger width, the locking element being aligned within the first level in the first position.

14. The device of claim 12, wherein the locking element is movably positioned within an opening that extends through the second member.

15. A medical device comprising:
a first member having an interior section formed by a sidewall, the interior section having a tapered portion that extends between a first level having a first width and a second level having a reduced second width;
a second member movable along the interior section and having a channel, the second member further including a flange that is wider than the interior section;
a biasing element positioned within the interior section and contacting against the second member to bias the flange towards the tapered portion;
a locking element sized to move within an opening in the second member, the locking element having a width greater than the opening;
a flexible elongated element that extends through the channel and outward beyond ends of the channel;
the second member movable relative to the first member between an unlocked position with the opening positioned in proximity to the first level with the locking element freely movable within the opening and the first and second members movable along the elongated element, and a locked position with the opening positioned in proximity to the second level with the locking element being forced into contact with the sidewall and extending outward into the channel and the first and second members fixed relative to the elongated element;
the flange is positioned outward from the first member in both the locked and unlocked positions.

16. The device of claim 15, further comprising a second locking element positioned within a second opening in the second member, the second locking element positioned in a common vertical plane with the locking element.

17. The device of claim 15, wherein the locking element includes a spherical shape.

18. The device of claim 15, wherein the elongated element extends along a centerline of both the first and second members.

19. A method of grasping a medical element comprising the steps of:
inserting the element through a channel within an inner member with the element extending outward from opposing ends of the channel;
inserting the inner member into a second channel that extends through an outer member and contacting the element against both the inner and outer members;
applying a force to an enlarged flange at a first end of the inner member with a width greater than the second channel and displacing the inner member longitudinally in a first direction relative to the outer member and moving a locking element along a tapered section of the outer member and forcing the locking element laterally toward the channel and into simultaneous contact with both the outer member and the element and locking the inner and outer members to the element, the flange positioned on an exterior of the second channel and a second end of the inner member positioned within the second channel of the outer member when the inner and outer members are locked to the element; and
displacing the inner member longitudinally in a second direction relative to the outer member and moving the locking element laterally away from the channel.

20. The method of claim 19, further comprising containing the locking element within the inner member when moving in the first and second directions.

21. The method of claim 19, further comprising displacing the inner member longitudinally in the first direction relative to the outer member and moving a second locking element laterally toward the channel, and displacing the inner member longitudinally in the second direction relative to the outer member and moving the second locking element laterally away from the channel.

22. A method of grasping a medical element comprising the steps of:
positioning an inner member and an outer member in an overlapping configuration with a section of the inner member with an enlarged flange extending outward beyond the outer member with the enlarged flange including a greater width than an interior of the outer member;
threading the element through the inner member and the outer member and into contact with both the inner and outer members;
moving the inner member to a first longitudinal position within the outer member with the enlarged flange spaced a first distance away from the outer member and positioning a locking element at a first level within an interior of the first member that includes an enlarged interior width to position the locking element away from the element and sliding the inner and outer members along a length of the element while the element is in contact with both the inner and outer members; and
moving the inner member to a second longitudinal position within the outer member with the enlarged flange spaced a second smaller distance away from the outer member and positioning the locking element at a second level within the interior of the first member having a reduced width and forcing the locking element into contact with the element and locking the inner and outer members to a specific location along the length of the element while the element is in contact with both the inner and outer members.

* * * * *